(12) United States Patent
Bonilla

(10) Patent No.: US 6,787,162 B1
(45) Date of Patent: Sep. 7, 2004

(54) METHOD AND COMPOSITION FOR REGULATION OF BLOOD CHOLESTEROL

(75) Inventor: Jose V. Bonilla, 804 Red River Rd., Gilbertsville, KY (US) 42044

(73) Assignee: Jose V. Bonilla, Gilbertsville, KY (US)

( * ) Notice: Subject to any disclaimer, the term of this patent is extended or adjusted under 35 U.S.C. 154(b) by 0 days.

(21) Appl. No.: 10/253,842

(22) Filed: Sep. 24, 2002

Related U.S. Application Data

(60) Provisional application No. 60/324,316, filed on Sep. 24, 2001.

(51) Int. Cl.$^7$ ............................................... A61K 35/78
(52) U.S. Cl. ...................... 424/725; 424/776; 424/489
(58) Field of Search ............................. 424/195.1, 725, 424/776, 777, 489

(56) References Cited

PUBLICATIONS

Simpson, G. E. Folk Medicine in Trinidad; Journal of American Folklore (1962) pp. 1–4 as reported by Napralert database acessed on Oct. 30, 2003).*

* cited by examiner

*Primary Examiner*—Patricia Leith
(74) *Attorney, Agent, or Firm*—King & Schickli, PLLC

(57) ABSTRACT

Novel methods and compositions for the control of elevated blood cholesterol concentrations are disclosed. The methods comprise administration of preparations derived from the seed of the Persea americana fruit. The compositions include powdered preparations and aqueous extracts. The compositions of the present invention may be administered orally by admixing with food or beverages, or may be provided as supplements in various forms.

11 Claims, No Drawings

METHOD AND COMPOSITION FOR
REGULATION OF BLOOD CHOLESTEROL

This application claims the benefit of U.S. Provisional Patent Application Ser. No. 60/324,316, filed Sep. 24, 2001.

TECHNICAL FIELD

The present invention relates to methods and compositions for the control of blood cholesterol. Specifically, the invention relates to a method for reducing elevated blood cholesterol and blood triglyceride concentrations in mammals, comprising administration of therapeutically sufficient amounts of preparations derived from the seed of the *Persea americana* fruit, and to compositions comprising these preparations.

BACKGROUND OF THE INVENTION

Elevated cholesterol is associated with a greater-than-normal risk of atherosclerosis and cardiovascular disease. Factors known to affect blood cholesterol include diet, body weight, physical activity or lack thereof, age, and sex. While cholesterol in normal amounts is a vital building block for essential organic molecules such as steroids, cell membranes, and bile acids, cholesterol in excess is known to contribute to cardiovascular disease. For example, cholesterol is a major element of plaque which collects in coronary arteries, resulting in cardiac disease.

Traditional therapies for reducing cholesterol include medications such as statins (which reduce production of cholesterol by the body). More recently, the value of nutrition and nutritional supplements in reducing blood cholesterol has received significant attention. For example, dietary compounds such as soluble fiber, vitamin E, soy, garlic, omega-3 fatty acids, and niacin have all received significant attention and research funding.

Despite the attention focused on traditional and alternative means for controlling blood cholesterol, blood triglycerides, and the like, the fact remains that it is estimated that greater than 50% of the population of the United States has cholesterol levels in the range of from 200–239 mg/dL, or what is considered borderline elevated. There thus remains a need in the art for alternative methods and compositions for reducing blood cholesterol, blood triglycerides, blood pressure, and the harmful effects thereof. The present invention satisfies this need in the art by providing a method for reduction of blood cholesterol and triglyceride concentrations. The invention further provides compositions for effecting reduction in blood cholesterol and triglyceride concentrations, in accordance with the methods described.

SUMMARY OF THE INVENTION

In accordance with the purposes of the present invention as described herein, a novel method is described for reducing blood cholesterol concentration and blood triglyceride concentration in a mammal. The invention is based on the surprising discovery that preparations derived from the seed of the *Persea americana* tropical fruit, also known as the avocado, provide an unexpected reduction in levels of blood cholesterol in individuals consuming them. Accordingly, the method of the present invention comprises administering a therapeutically effective amount of a preparation of the seed of *Persea americana*. The preparations of the present invention may be administered to any mammal wherein it is desired to reduce levels of blood cholesterol, including humans.

In one aspect of the present invention, the preparation may comprise a powder derived by the steps of slicing, crushing, or chopping the seed, drying the seed to a moisture content of up to 1%, and grinding the seed to reduce particle size. The seed may be dried by oven drying. Typically, the seed will be oven dried at 50 C to a moisture content of up to 1%. The dried seed preparation may then be ground to reduce particle size. Typically, the preparation will be ground to achieve a particle size of up to 1000 μm.

In another aspect, the present invention provides a method for reducing blood cholesterol concentration and blood triglyceride concentration in a mammal, comprising administering a therapeutically effective amount of an extract of the seed of *Persea americana*. It will be appreciated that any suitable extract for administration of the preparation of the present invention to a mammal may be used. Typically, the extract will be an aqueous extract derived by the steps of slicing, crushing, or chopping the seed of *Persea americana*, soaking the seed in water for at least 8 hours to form an extract, and filtering the seed to remove solids. The seed may also be macerated in water, such as by a conventional blender, prior to soaking and filtering. Typically, a ratio of water:seed of from about 5:1 to about 15:1 is used.

Typically, the method of the present invention comprises administration of from about 500 mg/day to about 2500 mg/day of the preparation of the seed of *Persea americana*. The preparation may be administered by admixing directly with food or beverages. Additionally, the preparation may be administered in any suitable supplement form, such as tablets, capsules, gelcaps, powders, suspensions, solutions, emulsions, liquid compositions, syrups, and the like. The manufacture of such means for administering a supplement is well known to those skilled in the art.

In yet another aspect of the present invention, a composition is provided for reducing blood cholesterol and blood triglyceride concentration in a mammal such as a human, comprising a therapeutically effective amount of a preparation of the seed of *Persea americana*. The preparation of the present invention may be formulated for administration as a powder or as an extract as described above. Typically, the composition is formulated to provide from about 500 mg/day to about 2500 mg/day of the preparation of the seed of *Persea americana*. As noted above, the compositions of the present invention may be directly admixed with food or drink for administration. The compositions may also be formulated for administration as a nutritional supplement, a vitamin supplement, a pharmaceutical preparation, a food additive, a food supplement, and the like. The manufacture of such supplements is well known to those skilled in the art. The composition of the present invention may be incorporated into the above forms as manufactured, or may be formulated with a pharmaceutically acceptable carrier.

Additional objects, advantages and other novel features of the present invention will become apparent to those skilled in this art from the following description wherein there is shown and described a preferred embodiment of this invention, simply by way of illustration of the modes currently best suited to carry out the invention. To achieve the foregoing and other objects, and in accordance with the purposes of the present invention as described herein, a novel method is described for reducing blood cholesterol in mammals.

In particular, the invention provides a method and a composition for reducing blood cholesterol in mammals such as humans, comprising preparations derived from the seed of the *Persea americana* tropical fruit. When admixed with food or drink or administered as a supplement, the compositions surprisingly reduce undesirably elevated concentrations of blood cholesterol in humans or animals consuming them, thereby improving overall health. As it will be realized, the invention is capable of other different embodiments and its several details are capable of modification in various, obvious aspects all without departing from the invention. Accordingly, the descriptions will be regarded as illustrative in nature and not as restrictive.

DETAILED DESCRIPTION OF THE INVENTION

In one aspect, the present invention provides a method for reducing blood cholesterol concentration and blood triglyceride concentrations in a mammal. Surprisingly, it has been discovered that preparations derived from the seed of the *Persea americana* tropical fruit provide an unexpected reduction in levels of blood cholesterol in individuals consuming them. Accordingly, the method of the present invention comprises administering a therapeutically effective amount of a preparation of the seed of *Persea americana*. In another aspect, the present invention provides compositions comprising the preparations of the *Persea americana* seed for reducing levels of blood cholesterol and blood triglycerides in individuals consuming them.

In one aspect, the preparations of the present invention comprise a dry, free-flowing powder suitable for direct admixture with foods, in drink, as a component of a meal replacement composition, or as a separate supplement. In another aspect, the present invention may be administered in the form of an aqueous extract derived from the *Persea americana* seed. In supplement form, the powder or extract of the present invention may be administered in any suitable form, such as a tablet, a capsule, a gel-cap, or a liquid.

The compositions embodying the present invention are preferably administered to individuals consuming them so as to provide the powder form of the invention in amounts ranging from about 500 mg to about 2500 mg per day, or an equivalent (dry weight) amount of seed extract. However, one of skill in the art will appreciate that the amount of the composition fed and the period of time over which the composition must be provided may vary in accordance with the body weight of the individual consuming it and the desired reduction in blood cholesterol to be achieved.

The following examples are intended to be illustrative of the invention, and are not to be considered restrictive of the scope of the invention as otherwise described herein. The examples demonstrate methods for deriving the preparations of the invention, and the surprising effect of the methods and compositions of this invention on reduction of blood triglycerides and blood cholesterol in individuals exhibiting both severe and mild hypercholesteremia.

EXAMPLE 1

Fresh seeds from the *Persea americana* tropical fruit were sliced and oven-dried at low temperature (50 C) for about 6 hours, until a moisture content of less than 1% was reached. The dried seed slices were then ground to a fine powder, resulting in a dried powder preparation. The powder was suitable for administration in this powder form by admixing directly to food or beverages. The powder was also administered by incorporating into capsules using methods well known in the art.

EXAMPLE 2

Seeds from the *Persea americana* tropical fruit was sliced and soaked in water overnight (water:seed ratio=10:1 w/v), then filtered to remove solids. The resulting aqueous extract was suitable for administration by admixing in food or drink, or as a separate supplement.

EXAMPLE 3

Seeds from the *Persea americana* tropical fruit are macerated directly in water using a blender for approximately 3 minutes (water:seed ratio of 10:1 w/v), then filtered to remove solids. The resulting aqueous extract may be administered as described in Example 2.

EXAMPLE 4

Twelve mildly hypercholesteremic individuals were selected to evaluate the effects of this invention. The selected individuals were not taking any conventional medications to control blood cholesterol. The composition of the present invention, prepared as described in Example 1, was administered by dissolving in fruit juice prior to administration. Each individual was provided 1000 mg of the powder composition of the present invention, administered every other day for a period of one month. Test subjects consumed their regular diets, and were not provided any specialized dietary treatments other than the composition of this invention.

Blood cholesterol was evaluated by the individual's primary care physicians using standard clinical laboratory test kits in accordance with the manufacturer's directions. As seen in Table 1, administration of the extract of this invention for a period of four weeks significantly reduced blood cholesterol concentrations and blood triglyceride concentrations, with reductions of up to 31% for cholesterol and 63.9% for triglycerides. Blood cholesterol for the test subjects was between 200 and 250 mg/dL prior to administration of the extract. After four weeks of administration of the extract of this invention, blood cholesterol in the test subjects had decreased to a range of from about 160 to about 200 mg/dL. No adverse side effects of consumption of the preparations of the present invention were noted during the test period.

| | | Baseline | | Four weeks | | diff./ | diff./ | Chol % | TGL % |
|---|---|---|---|---|---|---|---|---|---|
| P[1] | S[2] | Chol[3] | Tgl[4] | Chol | Tgl | Chol | Tgl | change | change |
| 1 | M | 263 | 533 | 238 | 202 | 25 | 331 | 9.051 | 62.101 |
| 2 | F | 252 | 159 | 226 | 109 | 26 | 50 | 10.318 | 31.447 |
| 3 | F | 302 | 244 | 268 | 367 | 34 | −123 | 11.258 | −50.409 |
| 4 | M | 266 | 187 | 228 | 173 | 38 | 14 | 14.286 | 7.487 |
| 5 | F | 316 | 524 | 271 | 239 | 45 | 285 | 14.241 | 54.389 |
| 6 | F | 161 | 443 | 154 | 160 | 7 | 283 | 4.347 | 63.883 |
| 7 | F | 290 | nd[5] | 200 | nd | 90 | | 31.035 | |
| 8 | M | 214 | nd | 150 | nd | 64 | | 29.906 | |
| 9 | M | 220 | nd | 180 | nd | 40 | | 18.181 | |
| 10 | M | 260 | nd | 220 | nd | 40 | | 15.384 | |
| 11 | F | 260 | nd | 200 | nd | 60 | | 23.076 | |
| 12 | F | 280 | nd | 220 | nd | 60 | | 21.429 | |

[1]Patient. Each patient was provided 1000 mg of a preparation, prepared as described in Example 1, every other day.
[2]Sex.
[3]Total blood cholesterol concentration, expressed in mg/dL.
[4]Total blood triglyceride concentration, expressed in mg/dL.
[5]Not determined.

EXAMPLE 5

One male test subject having mildly elevated levels of blood cholesterol was provided a daily dose of an aqueous extract providing 1000 mg of preparation of the seed of *Persea americana*, derived from fresh seeds as described in Example 2. As described in Example 4, the individual was not taking any conventional medications to control blood cholesterol. The subjects blood cholesterol was 250 mg/dL at initiation of the experiment. Four weeks after initiation of the experiment, the individual's blood cholesterol had decreased to 200 mg/dL.

EXAMPLE 6

Two severely hypercholesteremic female test subjects taking conventional medications for control of elevated blood cholesterol were selected. The individuals were unable to lower their cholesterol levels to normal levels even with the help of such medications. Additional side effects experienced by the individuals were headache and nausea. Conventional medications were discontinued seven days prior to initiation of the present experiments. Each test subject was provided 2000 mg of the powder-form preparation (prepared as described in Example 1) administered every other day. The powder was dissolved in fruit juice prior to administration for palatability and convenience. The test subjects were monitored by their primary physicians for total blood cholesterol concentration. Blood cholesterol was evaluated by the individual's primary care physicians using standard clinical laboratory test kits in accordance with the manufacturer's directions.

At the time the trial was initiated, the test subjects were experiencing blood cholesterol concentrations of up to 400 mg/dL. After 8 weeks of treatment, blood cholesterol had decreased to an average of 250 mg/dL. No adverse side effects of consumption of the compositions of the present invention were noted during the test period.

These results show that the compositions provided by the present invention, i.e. a preparation derived from the seed of the *Persea americana* fruit, effectively reduces blood cholesterol and blood triglycerides. The compositions of this invention were effective in reducing blood cholesterol in individuals experiencing both extremely elevated and mildly elevated blood cholesterol.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the extract could be produced using pharmaceutically and nutritionally suitable organic solvents, rather than the powdered form or aqueous extract as described herein. The seeds from which the preparations of this invention are obtained may be in any of a variety of forms, such as fresh, frozen, dessicated, or dried. Further, specific doses and forms of the composition of this invention maybe adjusted in accordance with the severity of the hypercholesteremia to be corrected, the needs of the individuals consuming the composition, the body weight of such individual, and the dietary preferences of such individuals. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitable entitled.

What is claimed is:

1. A method for reducing blood cholesterol concentration and blood triglyceride concentration in a hypercholesteremic mammal, comprising administering *Persea americana* seed powder in an amount of from about 500 mg/day to about 2500 mg/day to the hypercholesteremic mammal.

2. The method of claim 1, wherein said *Persea americana* seed powder is derived by the steps of slicing, crushing, or chopping the seed, drying the seed to a moisture content of up to 1%, and grinding the seed to reduce particle size.

3. The method of claim 2, wherein said powder is derived by the steps of slicing, crushing, or chopping the seed, oven drying the seed at 50° C. to a moisture content of up to 1%, and grinding the seed to reduce particle size.

4. The method of claim 1, wherein said mammal is a human.

5. The method of claim 1, wherein said *Persea americana* seed powder is administered by said seed powder directly with a food or beverage item.

6. The method of claim 1, wherein said *Persea americana* seed powder is administered in a form selected from the group consisting of a tablet, a capsule, a gelcap, a powder, a suspension, a solution, an emulsion, a liquid composition, a syrup, and any mixture thereof.

7. A method for reducing blood cholesterol concentration in a hypercholesteremic mammal, comprising administering *Persea americana* seed powder in an amount of from about 500 mg/day to about 2500 mg/day to the hypercholesteremic mammal.

8. The method of claim 7, wherein said mammal is a human.

9. The method of claim 7, wherein said preparation is administered by admixing directly with a food or beverage item.

10. The method of claim 7, wherein said preparation is formulated with a pharmaceutically acceptable carrier.

11. The method of claim 7, wherein said preparation is administered in a form selected from the group consisting of a tablet, a capsule, a gelcap, a powder, a suspension, a solution, an emulsion, a liquid composition, a syrup, and any mixture thereof.

* * * * *

UNITED STATES PATENT AND TRADEMARK OFFICE
CERTIFICATE OF CORRECTION

PATENT NO. : 6,787,162 B1
DATED : September 7, 2004
INVENTOR(S) : Jose V. Bonilla It is certified that error appears in the above-identified patent and that said Letters Patent is hereby corrected as shown below:

Column 6,
Line 30, please insert -- admixing -- before "said seed powder".

Signed and Sealed this

Twenty-eighth Day of June, 2005

JON W. DUDAS
*Director of the United States Patent and Trademark Office*